United States Patent
Alfano et al.

(10) Patent No.: US 7,033,348 B2
(45) Date of Patent: Apr. 25, 2006

(54) GELATIN BASED ON POWER-GEL™ AS SOLDERS FOR CR⁴⁺LASER TISSUE WELDING AND SEALING OF LUNG AIR LEAK AND FISTULAS IN ORGANS

(75) Inventors: Robert R. Alfano, Bronx, NY (US); Jing Tang, Arlington, MA (US); Jonathan M. Evans, New York, NY (US); Peng Pei Ho, Douglaston, NY (US)

(73) Assignee: The Research Foundation of The City University of New York, New York, NY (US)

( * ) Notice: Subject to any disclaimer, the term of this patent is extended or adjusted under 35 U.S.C. 154(b) by 0 days.

(21) Appl. No.: 10/119,914

(22) Filed: Apr. 10, 2002

(65) Prior Publication Data

US 2002/0198517 A1   Dec. 26, 2002

Related U.S. Application Data

(60) Provisional application No. 60/282,827, filed on Apr. 10, 2001.

(51) Int. Cl.
*A61B 18/18* (2006.01)

(52) U.S. Cl. ............ 606/8; 606/3; 606/9; 607/88; 607/89; 128/898

(58) Field of Classification Search .......... 606/3, 606/8, 9; 607/88–91; 128/898
See application file for complete search history.

(56) References Cited

U.S. PATENT DOCUMENTS

| | | | |
|---|---|---|---|
| 5,206,120 A * | 4/1993 | Hayashi | 430/376 |
| 5,409,479 A * | 4/1995 | Dew et al. | 606/9 |
| 5,552,452 A | 9/1996 | Khadem et al. | |
| 5,931,165 A * | 8/1999 | Reich et al. | 128/898 |
| 6,017,684 A * | 1/2000 | Miyake | 430/351 |
| 6,211,335 B1 | 4/2001 | Owen et al. | |
| 6,217,894 B1 | 4/2001 | Sawhney et al. | |
| 6,221,068 B1 * | 4/2001 | Fried et al. | 606/8 |
| 6,238,694 B1 * | 5/2001 | Gasco | 424/450 |
| 6,323,037 B1 | 11/2001 | Lauto et al. | |
| 6,391,049 B1 * | 5/2002 | McNally et al. | 606/214 |
| 6,607,522 B1 * | 8/2003 | Hamblin et al. | 606/8 |

(Continued)

OTHER PUBLICATIONS

Djagny KB, Wang Z, and Xu S. "Conformational Changes and some Functional Characteristics of Gleatin Esterified with Fatty Acid" PMID: 11409998, PubMed, Abstract.*

(Continued)

*Primary Examiner*—A. Farah
(74) *Attorney, Agent, or Firm*—Dilworth & Barrese LLP

(57) ABSTRACT

Laser tissue welding can be achieved using tunable $Cr^{4+}$ lasers, semiconductor lasers and fiber lasers, where the weld strength follows the absorption spectrum of water. The use of gelatin and esterified gelatin as solders in conjunction with laser inducted tissue welding impart much stronger tensile and torque strengths than albumin solders. Selected NIR wavelength from the above lasers can improve welding and avoid thermal injury to tissue when used alone or with gelatin and esterified gelatin solders. These discoveries can be used to enhance laser tissue welding of tissues such as skin, mucous, bone, blood vessel, nerve, brain, liver, pancreas, spleen, kidney, lung, bronchus, respiratory track, urinary tract, gastrointestinal tract, or gynecologic tract and as a sealant for pulmonary air leaks and fistulas such as intestinal, rectal and urinary fistulas.

17 Claims, 12 Drawing Sheets

U.S. PATENT DOCUMENTS

| | | | |
|---|---|---|---|
| 6,710,038 B1 * | 3/2004 | Hirai et al. | 514/54 |
| 2002/0002337 A1 * | 1/2003 | Alfano et al. | 600/476 |

OTHER PUBLICATIONS

Bass et al., "Laser Tissue Welding: A Comprehensive Review of Current and Future Clinical Applications", *Lasers in Surgery and Medicine*, 17:315-349 (1995).

Oz et al., "Tissue soldering by use of indocyanine green dye-enhanced fibrinogen with the near infrared diode laser", *J. Vasc. Surg.*, 11:718-25 (1990).

Moazami et al., "Reinforcement of Colonic Anastomoses With a Laser and Dye-Enhanced Fibrinogen", *Arch Surg.*, 125:1452-1454 (1990).

Wider et al., "Skin Closure with Dye-Enhanced Laser Welding and Fibrinogen", *Plastic and Reconstructive Surgery*, 88:1018-1025 (1991).

Chuck et al., "Dye-Enhanced Laser Tissue Welding", *Lasers in Surgery and Medicine*, 9:471-477 (1989).

Auteri et al., "Laser activation of tissue sealant in hand-sewn canine esophageal closure", *J. of Thoracic and Cardiovascular Surg.*, 103:781-783 (1992).

Sasajima et al., "Myristoyl Gelatin as a Sealant for Dacron Vascular Protheses", *Artificial Organs*, 21:287-292 (1997).

Choi et al., "Studies on Gelatin-Containing Artificial Skin: II. Preparation and Characterization of Cross-Linked Gelatin-Hyaluronate Sponge", *J. Biomed Mater. Res.*, 48: 631-639 (1999).

Takahashi et al., "Study on Hydrophilic Properties of Gelatin as a Clinical Wound Dressing: I. Hydrophilic Properties of Gelatin as a Wound Dressing", *J. Exp. Med.*, 40:159-167 (1993).

Lin et al., "Biological effects and cytotoxicity of the composite composed by tricalcium phosphate and glutaraldehyde cross-linked gelatin", *Biomaterials*, 19:905-917 (1998).

* cited by examiner

Glycin-Proline-Y    Glycine-X-Hydroxyproline $C_{13}H_{27}COOH$

Power-gel©

GELATIN BASED ON POWER-GEL™ AS SOLDERS FOR CR⁴⁺LASER TISSUE WELDING AND SEALING OF LUNG AIR LEAK AND FISTULAS IN ORGANS

CROSS REFERENCE TO RELATED APPLICATIONS

This application claims priority to U.S. provisional application Ser. No. 60/282,827 filed Apr. 10, 2001, the contents of which are hereby incorporated by reference.

GOVERNMENT RIGHTS

This invention was made with Government support from the Department of Energy, Center for Laser Imaging and Cancer Diagnostics, Grant #DE-FG02-98ER62560 (RF47997-00-03). The Government has certain rights in the invention.

BACKGROUND OF THE INVENTION

1. Field of the Invention

The present invention relates to specific lasers to be used in laser assisted tissue welding (LTW) and novel solders to be used in conjunction therewith that impart enhanced torque and tensile strength to tissue that has been sutured or sealed using LTW.

2. Description of the Related Art

In the past, damaged tissue was repaired using a variety of conventional sutures such as stitches or staples. More recently, the use of radiation, such as lasers, has been utilized to suture or weld tissue and seal leaks. Laser assisted tissue welding (LTW) can be achieved by directing a low energy laser beam of appropriate wavelength at the edges or surface of a tissue cut. The technique has gained the interest of the medical profession as an attractive new tissue repair procedure. In the LTW procedure, the wounded tissue is illuminated by radiation that directly or indirectly heats the tissue constituents, causing bonding to occur in the tissue structure and linking previously unattached tissues. Repair of damaged tissue can thus be achieved in greatly reduced time compared to that required by conventional suture techniques. Other advantages that this type of laser surgery has over traditional suture techniques have been reported, such as less foreign body reaction, less constriction, and reduced surgical time. While the LTW technique has found success in the experimental and clinical arenas, a wider usage is envisioned with further improvements in the procedure. In principle the LTW operation may be utilized wherever a tissue injury is present in an animal, including humans. However, it is especially suited to wounds to the skin, veins, arteries, respiratory tract, digestive tract, stomach, bladder and cervix.

Several investigators have worked on laser closure of wounds (White et al., Comparison of Laser Welded and Sutured Aortotomies, Arch Surg, 1986, 121:1133–1135 (1986); White, J. V., Laser Tissue Repair with the CO2 Laser, Poc SPIE, 1086 (1989); Oz et al., In Vitro Comparison of THC:YAG and Argon Ion Lasers for Welding of Biliary Tissue, Lasers Surg Med 9:248–253 (1989); White et al., Argon Laser Welded Arteriovenous Anastomoses, J Vasc Surg; 6:447–453 (1987)). Early contributions concentrated on welding tissues using lasers of different wavelengths applied directly to wound edges. Investigating the microstructural basis of the tissue fusion thus produced, Schober and coworkers proposed that there occurred a "homogenizing change in collagen with interdigitation of altered individual fibrils" (Schober et al., Laser Induced Alteration of Collagen Substructure Allows Microsurgical Tissue Welding, Science 232:1421–2, (1986)). These investigators, as well as others, proposed that the concentrated heating of the collagen fibrils above a threshold level allowed for their cross-linking (Goosey et al., Crosslinking of Lens Crystallins in a Photodynamic System: a Process Mediated by Singlet Oxygen, Science, 208:1278–1280 (1980); Chacon et al., Singlet Oxygen Yields and Radical Contributions in the Dye-sensitised Photo-oxidation in Methanol of Esters of Polyunsaturated Fatty Acids (Oleic, Linoleic, Linoleic and Arachidonic), Photochem Photobiol, 47:647–656, (1988); Tanzer, M. L., Cross-linking of Collagen, Science, 180: 561–6 (1973)). Unfortunately, the heat necessary to allow this reaction to occur causes collateral thermal damage. Even a slight distortion, in ocular tissue for example, may have functional consequences. Also, the event of laser weld failure, the edges of the tissues may be damaged by the original treatment and cannot be re-exposed to laser energy (Oz, et al., Tissue Soldering by Use of Indocyanine Green Dye-enhanced Fibrinogen with the Near Infrared Diode Laser, J Vasc Surg, 11:718–25 (1990)). As used herein, "solder" is a biological glue based on proteins and other compounds that can provide greater bond strength, lesser collateral damage, and a bigger parameter window for achieving a successful bond. Bass L S and Treat M R; Laser Tissue Welding: A Comprehensive Review of Current and Future Clinical Applications: Lasers in Surgery and Medicine, 17:315–349 (1995).

Further work attempted to enhance heat-activated cross-linking by placing a dye in the wound. It was reported that matching the absorbance of the dye with the laser wavelength allowed an adhesive effect to be achieved with less laser power output and collateral thermal injury (Chuck et al., Dye-enhanced Laser Tissue Welding, Lasers Surg Med, 9:471–477 (1989); Foote C S, In Free Radicals in Biology, W A Pryor, Ed. Vol 2, p. 85, Academic Press, New York, (1976); Oz et al., Indocyanine Green Dye-enhanced Welding with a Diode Laser, Surg Forum, 40:316–8 (1989)). Coupling the dye with a protein to create a tissue "solder" was also investigated. The protein of choice has been fibrinogen, and in particular autologous fibrinogen in order to avoid problems of the transfer of viral diseases through the use of blood components from pool donors. In previous applications, fibrinogen was obtained as a fraction of whole blood. It is not pure fibrinogen, but also contains other blood elements, such as clotting factors. Application of such a protein-dye mixture in various animal models proved to be an improvement to dye alone (Oz, et al., Tissue Soldering by Use of Indocyanine Green Dye-enhanced Fibrinogen with the Near Infrared Diode Laser, J Vasc Surg, 11:718–25 (1990); Moazami et al., Reinforcement of Colonic Anastomoses with a Laser and Dye-Enhanced Fibrinogen, Arch Surg, 125:1452–1454 (1990)). Unfortunately, human application was forestalled owing to the need to isolate the needed protein (fibrinogen) from the patient prior to the procedure to avoid the risks of contamination and infection from donor plasma.

Comparisons of protein-dye versus sutured closures have found the protein-dye group to produce less of an inflammatory response, result in greater collagen production, greater mean peak stress at rupture and better cosmesis (Wider et al., Skin Closure with Dye-Enhanced Laser Welding and Fibrinogen, Plastic Reconstr Surg, 88:1018–1025 (1991)).

Although several tissue adhesives have been formulated, few have seen widespread use clinically. Laser-activated tissue glues have been used in skin closures as well as vascular and bowel anastomoses (Chuck et al., Dye-enhanced Laser Tissue Welding, Lasers Surg Med, 9:471–477 (1989); Moazami et al., Reinforcement of Colonic Anastomoses with a Laser and Dye-Enhanced Fibrinogen, Arch Surg, 125:1452–1454 (1990); Wider et al., Skin Closure with Dye-Enhanced Laser Welding and Fibrinogen, Plastic Reconstr Surg, 88:1018–1025 (1991); Auteri et al., Laser Activation of Tissue Sealant in Hand-Sewn Canine Esophageal Closure, J Thor Card Surg, 103:781–783, (1992)). One of the more successful products thus far has been a mixture of cryoprecipitated fibrinogen and a dye that absorbs laser energy and releases it in the form of heat at the wound interface (Moazami et al., Reinforcement of Colonic Anastomoses with a Laser and Dye-Enhanced Fibrinogen, Arch Surg, 125:1452–1454 (1990); Oz et al., Tissue Soldering by Use of Indocyanine Green Dye-enhanced Fibrinogen with the Near Infrared Diode Laser, J Vasc Surg, 11:718–25 (1990)).

Several key areas have been identified in which improvements must be made before LTW becomes widely used for tissue repair. First, the bursting strengths of blood vessel anastomoses repaired by LTW must be improved since past bursting strengths have been found to be less than that using conventional suture repair. Secondly, unwanted aneurysm formation has been recorded in the range of 6–29% with traditional LTW. The tensile strength of existing protein solders themselves is insufficient to explain the recorded improvements and the role these solders play in laser assisted tissue repair.

As noted above, it is known that collagen fibers play an important role in LTW. Welding of the tissue may occur by fusion of the collagen fibers. Unfortunately, collagen cannot be dissolved in water directly. It only can be dissolved in acid, alkali or heavy salt solutions. Because its dissolution may damage the living welded tissue, there is no report of using collagen as a solder for LTW at present.

Gelatin is a collagen-degraded product that is water-soluble. It is an incomplete protein containing only a small number of the essential amino acids. Structurally, gelatin molecules contain repeating sequences of glycine-X-Y triplets, where X and Y are frequently the amino acids proline and hydroxyproline. Their sequences are responsible for the triple helical structure of gelatin and its intrinsic strength.

The physiochemical properties of gelatin may be modified using processes such as myristoylation and silanization. For example, myristoyl gelatin retains its gel structure at temperatures above body temperature without any crosslinking, and can be used as a sealant for Dacron™ vascular prostheses [Sasajima et al, Myristoyl Gelatin as a Sealant for Dacron Vascular Prostheses. *Artificial Organs* 1997; 21:287–292].

The use of tissue glues in conjunction with lasers or some other form of photoactivating radiation is known. For example, U.S. Pat. No. 5,552,452 discloses an adhesive of a biocompatible peptide in combination with a flavin photosensitizer that forms an adhesive upon photoactivation.

Similarly, U.S. Pat. No. 6,323,037 claims a composition for tissue welding that contains an active compound, which can be a protein or peptide such as albumin, collagen, myoglobin and fibrinogen, a solvent, and an energy converter. Preferred energy sources are lasers such as Nd:YAG lasers, GaAlAs lasers, Argon lasers and $CO_2$ lasers.

U.S. Pat. No. 6,211,335 claims a fluid protein solder in a solvent that can optionally include a dye. The preferred protein to be used in the solder is albumin.

U.S. Pat. No. 6,217,894 claims a compliant tissue sealant that has polymerizable groups that are highly adherent to the surface, e.g. tissue, to which it is applied. The monomers may include hydrophilic regions consisting of proteins such as gelatin, collagen, albumin, ovalbumin, or polyamino acids.

In the past, certain specified lasers have been used in tissue suturing or welding. For example, U.S. Pat. No. 6,221,068 discloses the use of pulsed delivery of radiation, such as from an Nd:YAG laser, in combination with a dye to weld tissue containing proteins, especially collagen.

It would be beneficial to develop a solder for use in conjunction with laser assisted tissue welding that would have enhanced tensile and torque strength. Methods for welding tissue should have minimal adverse effects on surrounding tissue.

SUMMARY OF THE INVENTION

This invention pertains to enhancements in the LTW procedure and post-procedure effectiveness by addressing the light source utilized in the operation and by the implementation of biological solders to enhance tissue weld strength.

This invention discloses the use of specified wavelengths of $Cr^{4+}$ laser beams that have been found to be readily absorbed by water in tissue to heat both tissue and the solders for tissue welding and sealing.

This invention also discloses new biological solders based on collagen-degraded products, such as gelatin. In a preferred embodiment, gelatin is esterified, using an active ester method, resulting in a new gelatin based solder called Power-gel™. Power-gel™ enhances the tensile and torque strength of laser welded tissue. Its melting point is 39° C., higher than that of gelatin (~35° C.) and the human body temperature (37° C.), so it does not melt at human body temperatures.

Methods for sealing and welding tissue using these lasers and solders are also disclosed.

BRIEF DESCRIPTION OF THE DRAWINGS

In the drawings herein, like reference numerals represent like parts.

DETAILED DESCRIPTION OF PREFERRED EMBODIMENTS

Figure 1:
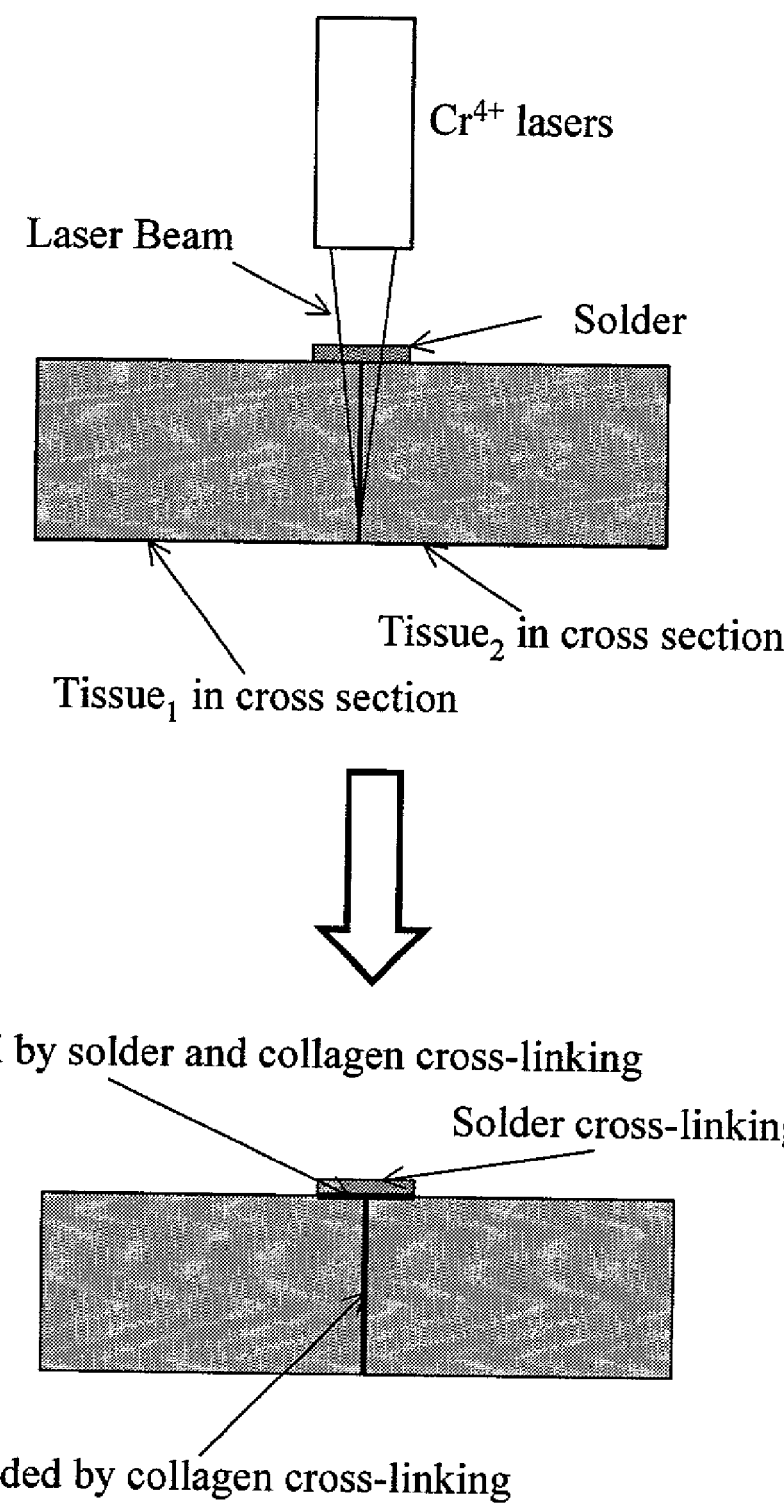
FIG. 1 is a schematic diagram of a mechanism for $Cr^{4+}$ laser tissue welding with gelatin and Power-gel™.

The present invention is based, in part, on the premise that the choice of light source and solder utilized in optical tissue welding procedures, such as LTW, play a role in the effectiveness of the technique to achieve practical tissue repair. The interaction of itissue with light is governed by the optical parameters of tissue, including scatter and absorption, which in turn are dependent on the wavelength of the incident light. Under certain circumstances light energy that is converted to heat in tissue will cause binding of adjacent tissue constituents, such as collagen, thereby achieving tissue repair. This process may be refined using the appropriate light source and delivery system best matched to the particular tissue at hand.

There are many types of tissue in the body that differ in their optical properties, such as absorption, scatter and reflectivity. The interaction of a particular tissue with the incident radiation is of paramount importance in the effectiveness of the LTW operation. It is therefore desirable to have a light source that can be modified to suit the particular type and thickness of the tissue to be repaired.

This invention involves tailoring the light source to the tissue under repair. In particular, light in the near-infrared (NIR) spectral region that coincides with a resonance in the absorption spectrum of water has been identified as being convenient for the LTW process. Since water makes up a significant percentage of living tissues, it therefore has an important role in the absorption properties of tissue. The variation in the penetration depth is a function of the change in water absorption maximum to minimum over the tuning range of the light source.

By implementing a light source that is tunable over the spectral region of water absorption, the depth to which the incident light can penetrate a tissue can be selected. The 1.2–1.6 μm wavelength range is particularly attractive for LTW applications as a large change in water absorption is experienced in this region. Strong absorption in the 1.4 μm region has a tissue penetration depth of ~0.1 mm while light at 1.3 μm may penetrate more deeply to 5 mm into the tissue. This large degree of penetration depths makes it feasible to optimize the welding process for a wide variety of tissue types.

In addition, by utilizing the appropriate wavelength, the absorption and scattering properties of the tissue can be exploited to yield strong fusion of the tissue upon the illumination. For instance, if a shallow wound is to be treated, light of a wavelength that is strongly absorbed by the tissue is preferable because a large percentage of the light will be absorbed in the damaged region making the operation more efficient, and minimizing the light absorbed in other regions, thereby reducing any secondary injury to underlying tissue. For a deeper wound, light that is less strongly absorbed is desirable to ensure that sufficient light for welding reaches the depth of the injury. Light in the NIR spectral region is especially desirable for this operation: the wavelengths in this region may be tuned continuously over a range of penetration depths in tissue from about ~0.1 mm to about 5 mm.

Laser light in near infrared has unique properties that make it attractive for tissue welding and sealing applications. Laser light has a high degree of brightness and directionality as compared to other light sources. This means that tighter focal spots may be created with higher positioning accuracy using laser light than light from other sources. It is desirable for practicality to operate with a single source of intense light that may be tuned over the NIR spectral region from 800 nm to 3000 nm. Possible such sources are lasers based on the active ion $Cr^{4+}$ in hosts, semiconductor lasers and fiber lasers. Suitable semiconductor lasers include InGaAs and In GaAsP alloy semiconductor lasers, and AlGaAs quantum well (QW) intraband transition semiconductor lasers. Suitable fiber lasers include Yb (Ytterbium) doped fiber lasers and Er (Erbium) doped fiber lasers. These lasers may be tuned to a spectral range which corresponds to the absorption band of water in tissue permitting the welding or sealing of tissue without additional tissue solders or dyes.

In a preferred embodiment, tunable near-infrared (NIR) lasers based upon the $Cr^{4+}$-active ion, such as, Cr:forsterite lasers with wavelengths tunable from about 1,150 to about 1,350 nm, Cunyite $Cr:Ca_2GeO_4$ lasers tunable from about 1,350 to about 1,500 nm, and $Cr^{4+}$ YAG lasers tunable from about 1,370 to about 1,600 nm, which have not previously been used for tissue welding, are used. The unique tuning ranges of these lasers make them attractive as light sources for the tissue welding technique as their simplicity of operation negates the need for the addition complexity of wavelength conversion processes that are required to generate light in the NIR from other lasers. Moreover, tissue welding may be possible using the absorption bands of water in the 1,150 to 1,600 nm spectral region without additional dyes. The tunable wavelengths from the $Cr^{4+}$ lasers also offer more versatility in selecting precise depth penetration for laser tissue welding.

The $Cr^{4+}$ lasers emit radiation in the NIR desired spectral range, where there is less scattering and deeper penetration than for visible light, such as Argon (1 to 2 mm) and other lasers, including Nd:YAG lasers (3 to 4 mm) and $CO_2$ laser (0.02 mm). These $Cr^{4+}$ laser beams have penetration depths varying from 2 to 5 mm depending on their wavelengths, which can heat water and adipose in the tissue and solders to induce binding of collagen and elastin. These $Cr^{4+}$ lasers may be suitable for thin-walled tissue, such as small blood vessel anastomoses, as well as for thicker-wall tissue welds, such as skin, digestive tubes and the urinary system, when the appropriate wavelength is chosen. The two lasers can be tuned to various wavelengths from 1,150 to 1,500 nm. Output of these lasers has several key advantages over single-wavelength lasers. The irradiation can be tuned to the absorption bands of different tissue constituents, such as, the 1,203 nm band for adipose, and the 1,350 nm band for water. In addition, their second harmonic output (575–750 nm) can be turned to the hemoglobin band in blood vessels. Different kinds of tissues can be welded by selecting different NIR wavelengths. An additional advantage in the use of these lasers is utilizing quartz fiber optics to deliver the beams, which a surgeon can operate easily.

The tunable lasers described above can be used for tissue welding utilizing the absorption of water to heat the tissue. When used without solder, different welding results are obtained for lasers under the same conditions using different NIR wavelengths. These results show that the greater the water absorption, the higher the tensile strength of laser-welded tissue. The tunable wavelengths from the $Cr^{4+}$ lasers offer more versatility in selecting precise depth penetration for LTW. While the $Cr^{4+}$ lasers, semiconductor lasers, or fiber lasers may be used alone, they may also be used in combination with dyes or tissue solders in the welding and/or sealing process.

In one embodiment of the present invention, gelatin is used as a solder glue for LTW procedures. The mechanism by which the laser and gelatin-based solder works is that the laser beam first heats the tissue due to the absorption bands of water in the welded tissues. Heated tissue facilitates the bonding of molecules in native tissue proteins, such as collagen, as well as the added protein from the solder to achieve tissue bonding and repair. The gelatin-based solder of the present invention may be used with any known laser used in laser assisted tissue welding. In preferred embodiments, the gelatin-based solder is used with $Cr^{4+}$ lasers, semiconductor lasers, or fiber lasers. While gelatin lacks an absorption peak in NIR, the $Cr^{4+}$ laser beam absorbed by water remedies this defect.

There are several other key characteristics of gelatin that make it an attractive solder for LTW, including:

1. It can be completely resorbed by the human body;
2. It has not shown any antigenicity and sensitization to humans [Choi et al, Studies on Gelatin-Containing Artificial Skin: II. Preparation and Characterization of Cross-Linked Gelatin-Hyaluronate Sponge. *J Biomed Res (Appl Biomater)* 1999; 48:631–639.];
3. It has been used in a wide variety of wound dressing [Takahashi et al, Study on "Hydrophilic Properties of Gelatin as a Clinical Wound Dressing. I. Hydrophilic Properties of Gelatin as a Wound Dressing" *Tokushima J Exp Med* 1993; 40:159–167, and Lin et al, Biological Effects and Cytotoxity of the Composite Composed by Tricalcium Phosphate and Glutaraldehyde Cross-Linked Gelatin. *Biomaterials* 1998; 19(10): 905–17];
4. Its physicochemical properties can be suitably modulated due to the existence of many functional groups (glycine, proline, hydroxyproline, glutamic acid, arginine, aspartic acid, and other amino acids); and
5. With sterilization, gelatin can be safely used in the human body without the dangers of contamination and viral infection.

In a preferred embodiment of the present invention, gelatin has been refined for more advantageous performance as a LTW solder. It has been found that gelatin and esterified gelatin can be used as solders in conjunction with laser tissue welding to impart to tissue tensile and torsion strengths much greater than that of an albumin solder. The presence of a biological solder, such as the gelatin-based solder of the present invention, at the site of the damaged tissue during tissue welding enhances the strength of the tissue post-welding compared with tissue where there is no solder present. The biological solder is applied to the edges of a tissue wound and is activated by an increase in its temperature caused by irradiating the wound with the incident light from a laser. Heated tissue facilitates the bonding of native tissue protein present in the tissue surrounding the wound as well as any added protein solder to achieve tissue repair. Using solders of intrinsically high tensile and torsion strength enhances the post-welded tissue strength.

In a preferred embodiment, the gelatin has been esterified using an active ester method, an organic synthesis method known to those skilled in the art that involves the use of fatty acids such as myristic acid. In a preferred embodiment, myristic acid is added to the gelatin in amounts ranging from about 0.25% to about 10% by weight (w/w), preferably about 0.5% to about 5% (w/w) at 60° C. for one hour to produce an esterified gelatin called Power-gel™.

The mechanism of $Cr^{4+}$ laser with gelatin or Power-gel™ is that $Cr^{4+}$ laser beam heats up the tissue due to the absorption bands of water. Heated tissue facilitates the bonding of native tissue protein, such as collagen, as well as added protein solders, gelatin or Power-gel™, to achieve tissue repair. With the addition of gelatin or Power-gel™ as a solder, improving the tensile strength of welded tissues is achieved. In general, the bonding process may be described as follows:

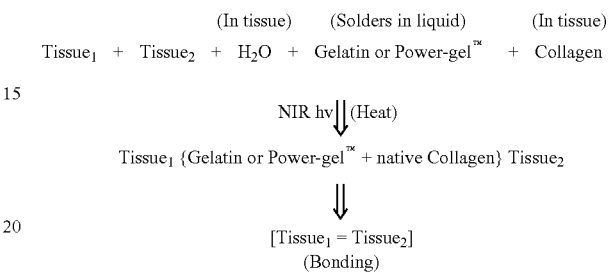

In a preferred embodiment, the solder (gelatin or Power-gel™) is applied in liquid form over the surface of the tissues to be connected ($Tissue_1$ and $Tissue_2$), about 0.1 to 0.15 mm thickness, before welding (FIG. 1). The edges of the tissue wound are joined and a NIR beam from a $Cr^{4+}$ laser irradiates the solder and penetrates through it to the tissues. The energy is absorbed by water in the tissues and the solder, which are heated to a temperature above 60° C. Native collagen in the tissues is denatured and cross-linking then occurs between the solder and denatured collagen. $Tissue_1$ and $Tissue_2$ are bonded together due to the cross-linking of the solder, collagen and the combined solder with collagen found at the junction of welded tissues.

The present invention also relates to a method of achieving the repair of tissue(s) through the irradiation of said tissue(s) with light of appropriate intensity and wavelength in the presence or absence of a biological solder. In a preferred embodiment, the following steps are used in tissue repair: (a) (optional) applying a solder to the site of the damaged tissue, (b) joining the edges of a tissue wound, (c) illuminating at least a portion of the damaged tissue with light that is tunable or fixed to a wavelength that is selected on the basis optical properties of the tissue and the anatomy of the wound, (d) activating the native proteins in the illuminated tissue as well as any protein solder present to form bonds in the damaged tissue and achieve tissue repair, (e) suspending any further illumination to prevent damage to the repaired tissue.

The methods of tissue welding can be used to both suture and seal body tissues in the course of known medical procedures such as conventional surgery and endosurgery. For example, the methods of the present invention can be used to seal pulmonary air leaks and fistulas in the gastrointestinal tract, such as intestinal and urinary fistulas. The methods of the present invention may also be used to seal or weld animal or human tissue including, but not limited to, wounds to the skin, mucosal tissue, bone, blood vessels, neural tissue, hepatic tissue, pancreatic tissue, splenic tissue, renal tissue and bronchial tissue as well as other tissues of the respiratory tract, urinary tract, gastrointestinal tract and gynecologic tract.

In order for the invention to be better understood, the following examples are given by way of illustration only.

EXAMPLE 1

Preparation of the solders: gelatin, Power-gel™, and albumin.

1. 33% gelatin. Gelatin powder from bovine skin with 225 bloom was added with 1× phosphate-buffered saline (PBS, pH 7.4). It was heated at 50° C. to become a liquid before use.

Figure 2:
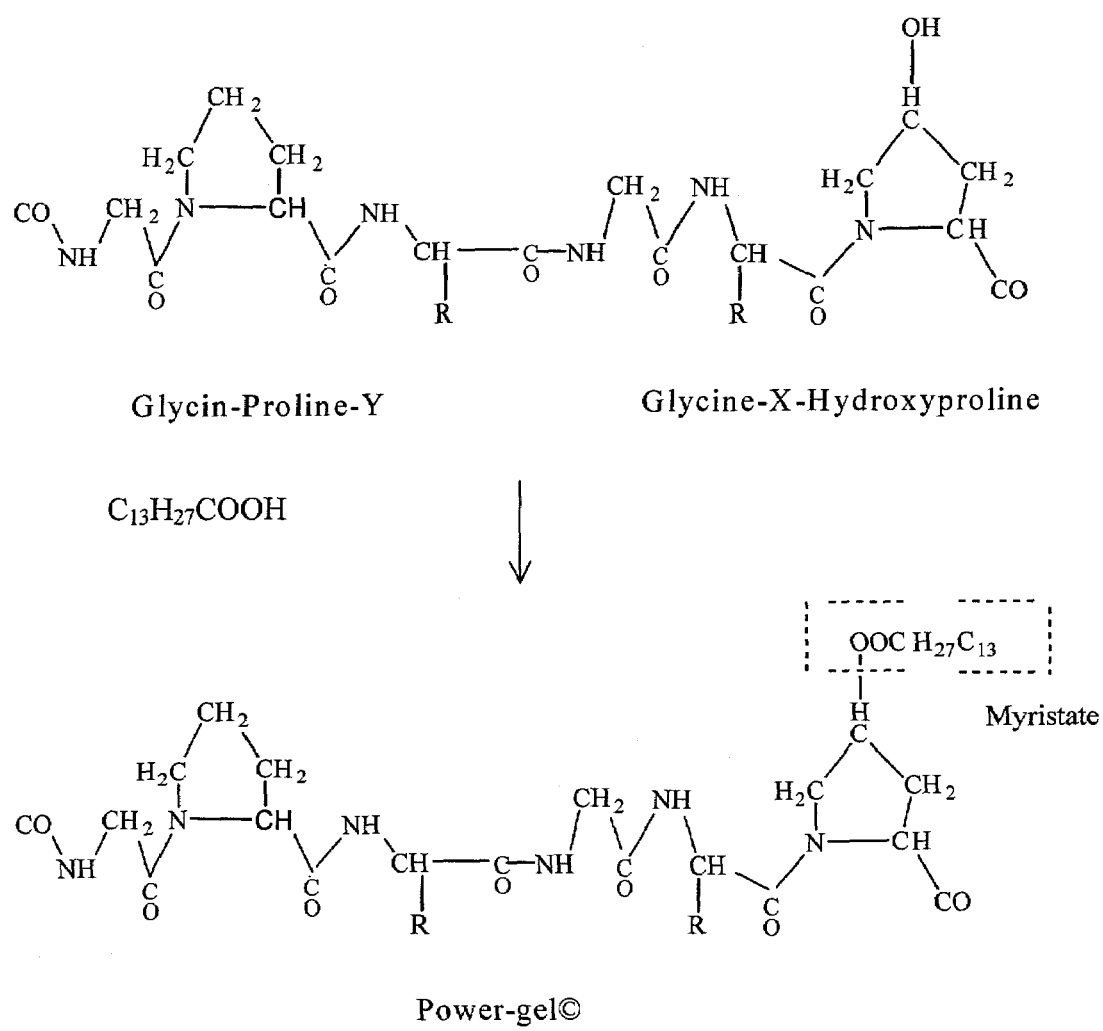
FIG. 2 illustrates representative structures of gelatin and Power-gel™, as well as their chemical action.

2. Power-gel™. Power-gel™ was formed by introducing mynistic acid into gelatin powder. The gelatin was combined chemically with myristic acid (CHCOOH), using an active ester method. One wt % (w/w) of aqueous solution of myristic acid was prepared at 60° C. using double distilled water under gentle stirring for 30 min. Then gelatin powder was added in the solution slowly. Myristoylation was performed in a water bath and under gentle stirring for one hour. The chemical action was performed in aqueous media at a low temperature to avoid side reaction and degradation of gelatin, but higher than the melting point of myristic acid (55° C.). The formula for Power-gel™ is shown in FIG. 2. Different concentrations of myristic acid were added to get the best tensile and torque strengths. In aqueous solution, the Power-gel™ occurred at a concentration of 33 mg/ml or higher, and melting point of the gel was 39° C. It was heated at 50° C. to become a liquid before used.

3. 50% albumin (as control). A stock of 30% bovine albumin solution was further concentrated by adding bovine serum albumin powder to provide a concentration of 50%.

EXAMPLE 2

Figure 3:
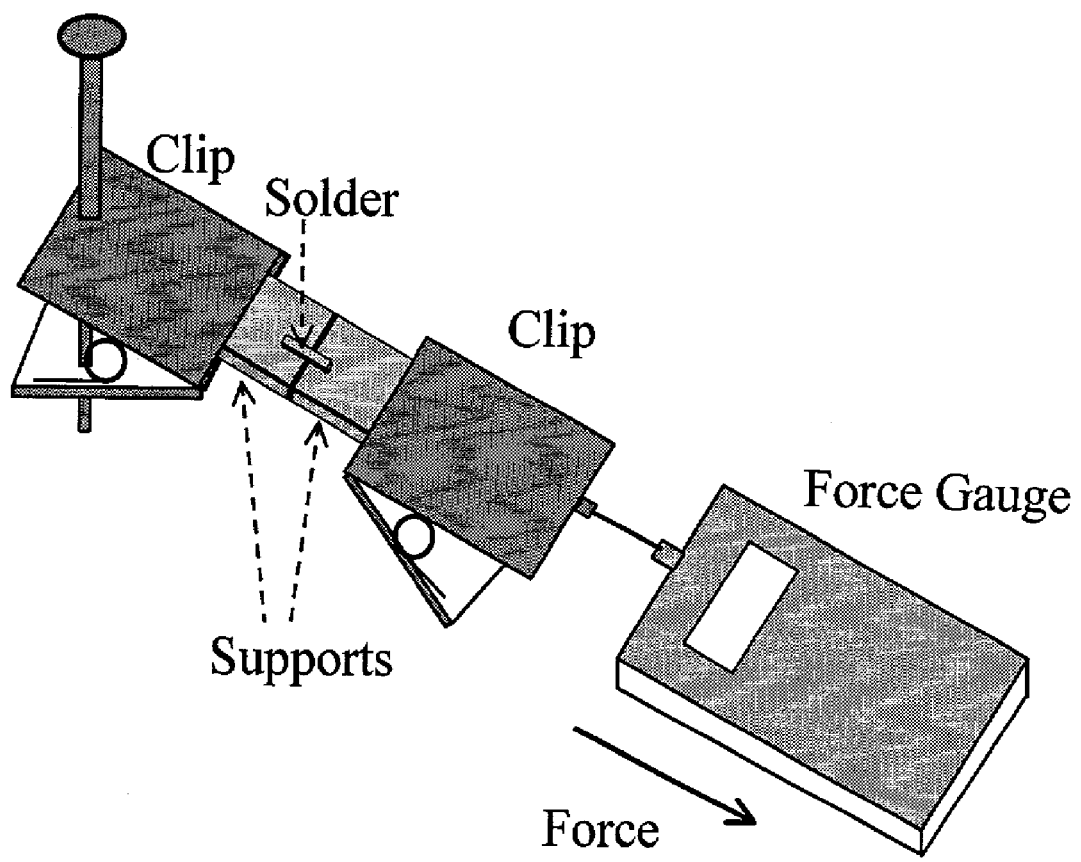
FIG. 3 is a schematic diagram of a tensile strength measurement apparatus for solders.

A paperboard with a thickness of 0.1 mm was used as a support for the solder strength test. Solders prepared in accordance with Example 1 were mounted horizontally between two supports with a thickness of 0.15±0.05 mm. The paperboard with solder was then put into an oven with supports for heating at 80° C. for 2 min as an imitation of laser heating. The tensile strength of the solders were tested with a digital force gauge. The apparatus by which the tensile strength was tested is set forth in FIG. 3. The digital force gauge was connected to one support, while the other was fixed (see FIG. 3). The tension force parallel to the solder was applied until the solder broke. The maximum force was recorded automatically. The length and width in the surface of the broken solder was measured with a digital micrometer. The broken surface was calculated as length multiplied by width.

Figure 4:
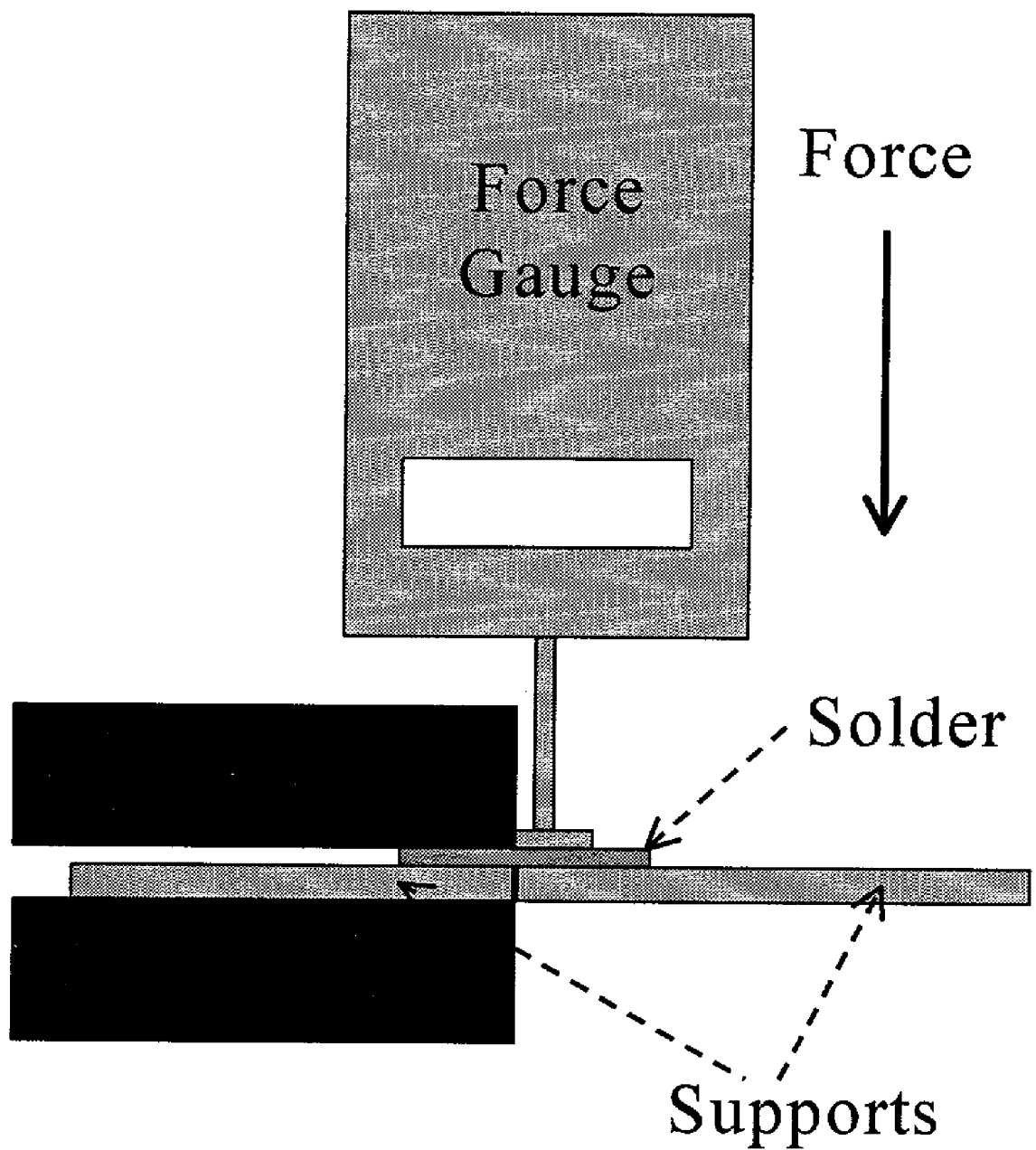
FIG. 4 is a schematic diagram of a torque strength measurement apparatus for solders.

The torque strength of the solders prepared in accordance with Example 1 were tested by the apparatus shown in FIG. 4. The solders were mounted on the supports and heat-treated with the same methods as described above. A force vertical to the solder was applied, until the solder broke. The length and width of the surface of the broken solder was measured. The surface was calculated as length multiplied by width.

The tensile and torque strengths under humid conditions were also measured. The solder with the supports was kept in a water bath (98 to 100% humidity) at 37° C. for 24 hrs, before tensile and torque strengths were measured as described above.

Figure 7:
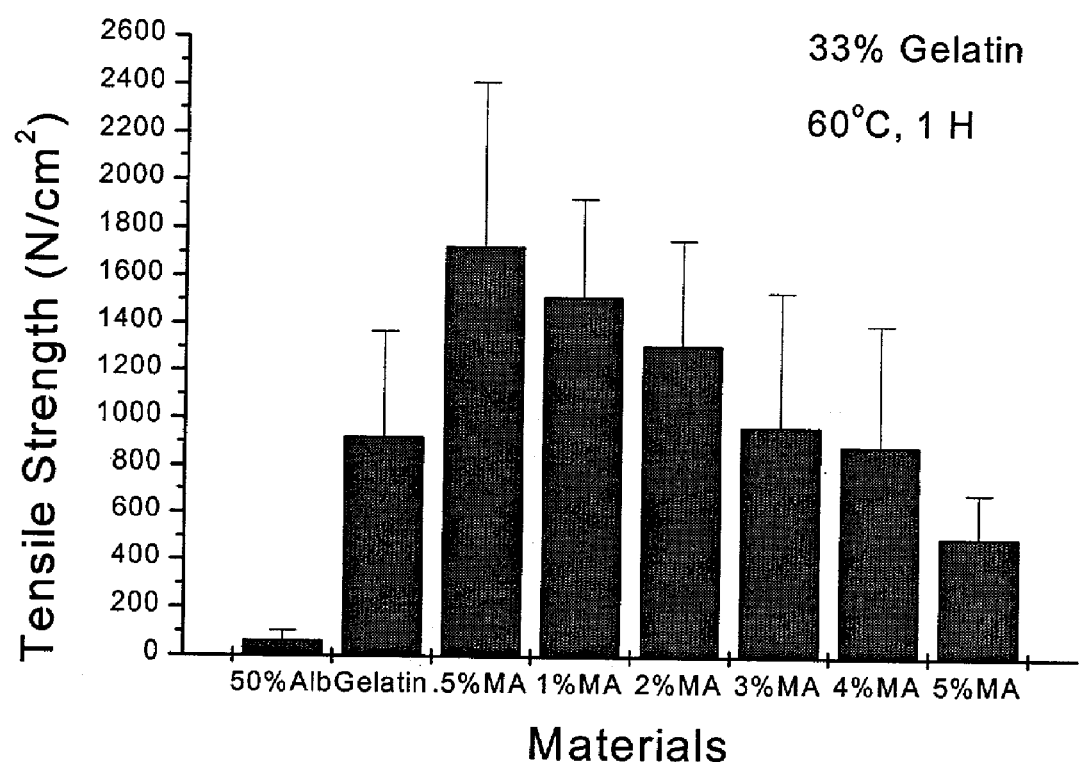
FIG. 7 is a chart showing the relationship of different myristic acid concentrations and solder tensile strengths.
Figure 8:
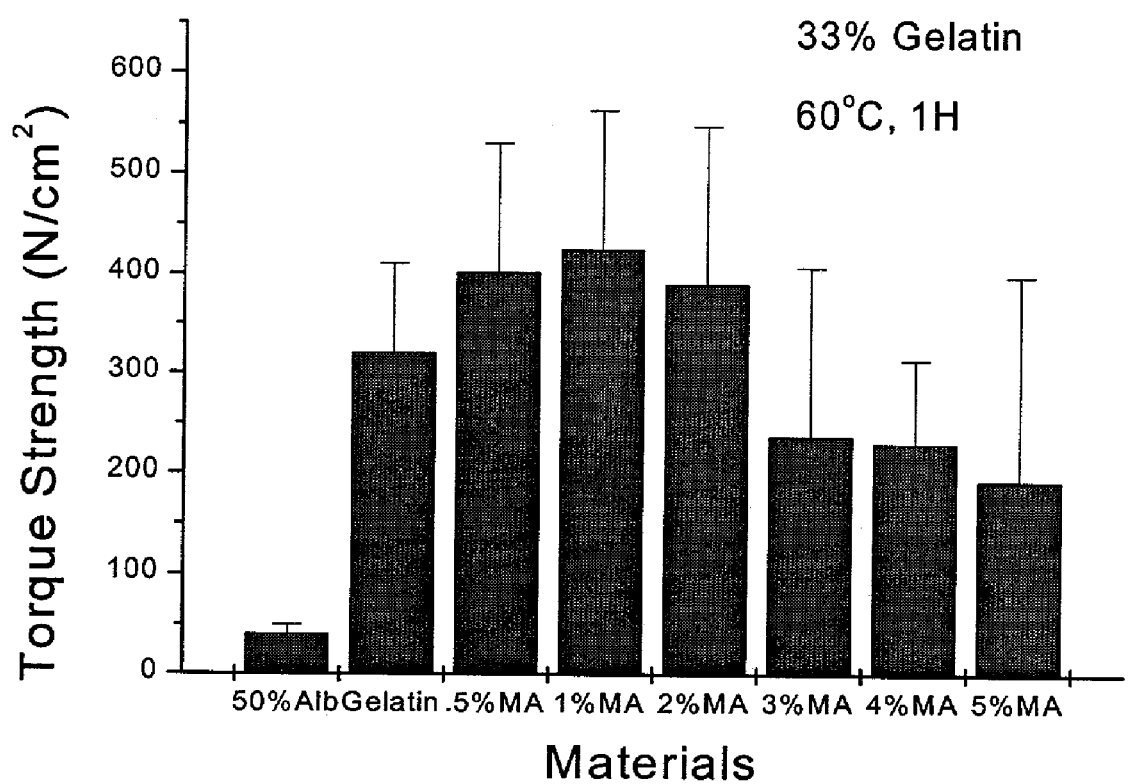
FIG. 8 is a chart showing the relationship of different myristic acid concentrations and solder torque strengths.

The obtained tensile and torque strengths with different concentrations of myristic acid prepared at the temperature of 60° C. for one hour are shown in FIG. 7 and FIG. 8, separately. 1% myristic acid was chosen to develop the Power-gel™, even though the group prepared with 0.5% myristic acid obtained the strongest tensile strength, but no statistical difference with the 1% myristic acid group. The melting point of Power-gel™ was 39° C. The other physiochemical properties, compared with other solders, are discussed below.

Figure 9:
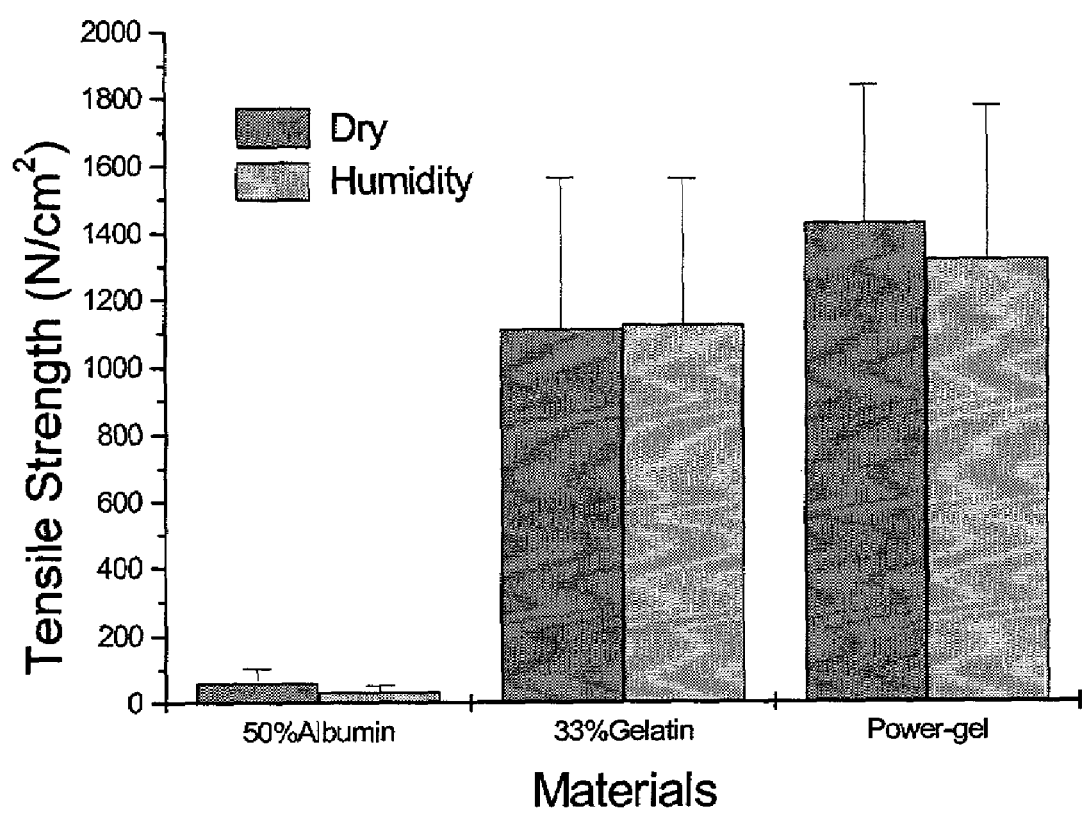
FIG. 9 is a chart showing the tensile strengths of albumin, gelatin, and Power-gel™ in dry and humid conditions.

The tensile strength results (n=20 for each group) of 50% albumin, 33% gelatin, and Power-gel™ in dry and in humid conditions are shown in FIG. 9. The average initial post-heated tensile strength values were 62.56±40.50 N/cm$^2$ for albumin, 1111.43±449.01 N/cm$^2$ for gelatin and 1428.15±405.92 N/cm$^2$ for Power-gel™. Power-gel™ had the best tensile strength with a statistical significance, compared with the gelatin and albumin (t=2.340, p<0.05, and t=14.971, p<0.01, respectively). After being subjected to humidity for 24 hrs, the average tensile strength values were 21.35±9.27 N/cm$^2$ for albumin, 1124.06±433.18 N/cm$^2$ for gelatin and 1319.82±456.78 N/cm$^2$ for Power-gel™. Albumin exhibited a decrease in its tensile strength (t=5.66, p<0.01). Gelatin exhibited an increase in its tensile strength (t=2.1675, p<0.05). Power-gel™ retained its tensile strength (see FIG. 9).

Figure 10:
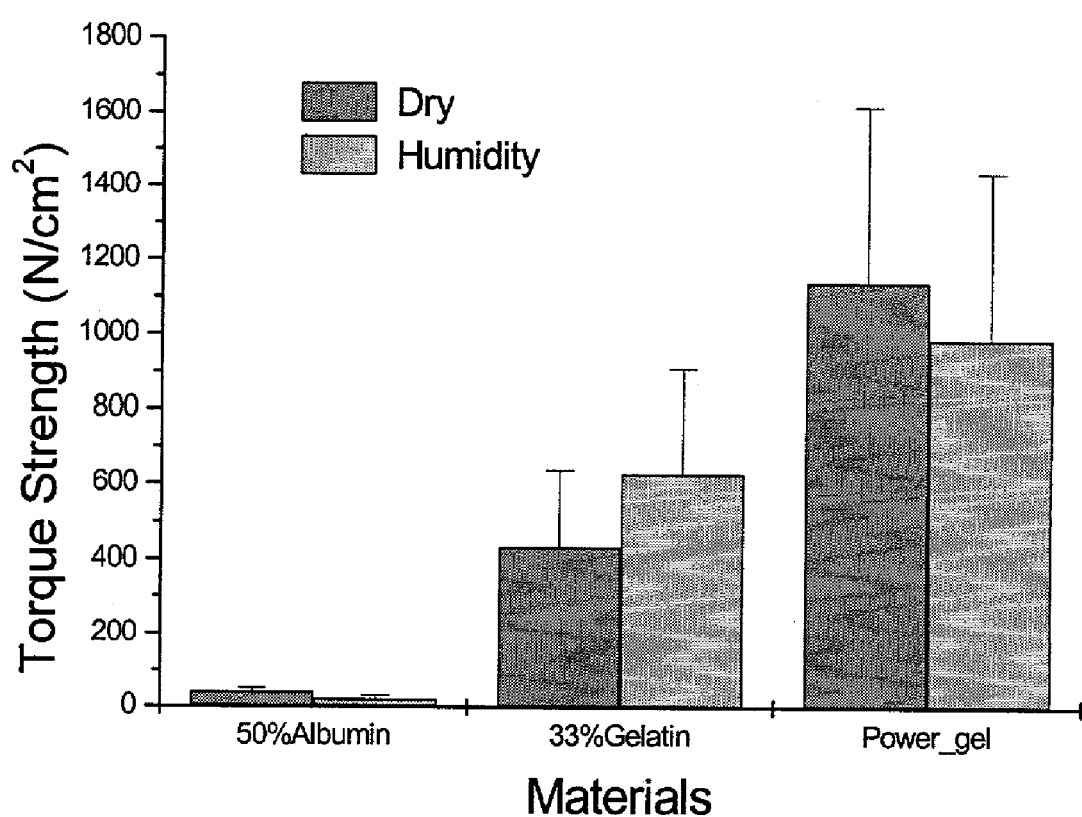
FIG. 10 is a chart showing the torque strengths of albumin, gelatin, and Power-gel™ in dry and humid conditions.

The torque strength results (n=20 for each group) of 50% albumin, 33% gelatin, and Power-gel™ in dry and humility conditions are shown in FIG. 10. The average initial post-heated tensile strength values were 40.66±8.56 N/cm$^2$ for albumin, 434.73±202.71 N/cm$^2$ for gelatin and 907.53±493.33 N/cm$^2$ for Power-gel™. Power-gel™ had the best tensile strength with a statistical significance, compared with the gelatin and albumin (t=2.308, p<0.05, and t=4.339, p<0.01, respectively).

After being subjected to humidity for 24 hrs, the average torque strength values were 33.91±9.27 N/cm$^2$ for albumin, 628.47±280.98 N/cm$^2$ for gelatin and 987.30±450.19 N/cm$^2$ for Power-gel™. Albumin exhibited a decrease in its tensile strength (t=2.1675, p<0.05). There were no changes in the tensile strength of Gelatin or Power-gel™ (see FIG. 10).

EXAMPLE 3

The gelatin and Power-gel™ were mounted on microscope slides with a thickness of 0.25±0.10 mm and a surface of approximately 15×25 mm. After heating at 80° C. for 2 min, the solder on the slide was weighed and immersed in PBS at 25° C. for 24 hrs. The solder and slide were re-weighed after removal from PBS. Water uptake ability was calculated according to the following equation:

$$\text{Water content (\%)} = [(W_w - W_d)/W_w] \times 100,$$

Where $W_d$ is the weight of the dry solder and $W_w$ is the weight of the wet solder.

Differences in the tensile and torque strengths (n=20 for each group) were compared by an analysis of one side variance (ANOVA) and a Student's t test. A p-value of <0.05 was assumed to represent a significant difference.

The average Water uptake ability measurement is 96.1±0.8% for gelatin and 94.6±0.1% for Power-gel™ (n=12 for each group). This shows an increased water uptake of up to 27 times for gelatin and 18 times for Power-gel™. There is a statistical significance between them (t=3.77921, p<0.01).

EXAMPLE 4

Forsterite and Cunyite lasers, tunable near-infrared lasers based upon the $Cr^{4+}$-active ion that are capable of providing continuous beams of radiation, were used in this example. The emission wavelengths of the Forsterite laser were tuned from 1,130 to 1,370 nm with maximal power output of 350 mW. The emission wavelengths of the Cunyite laser were tuned from 1,350 to 1,500 nm with a maximal power output of 420 mW.

Figure 5:
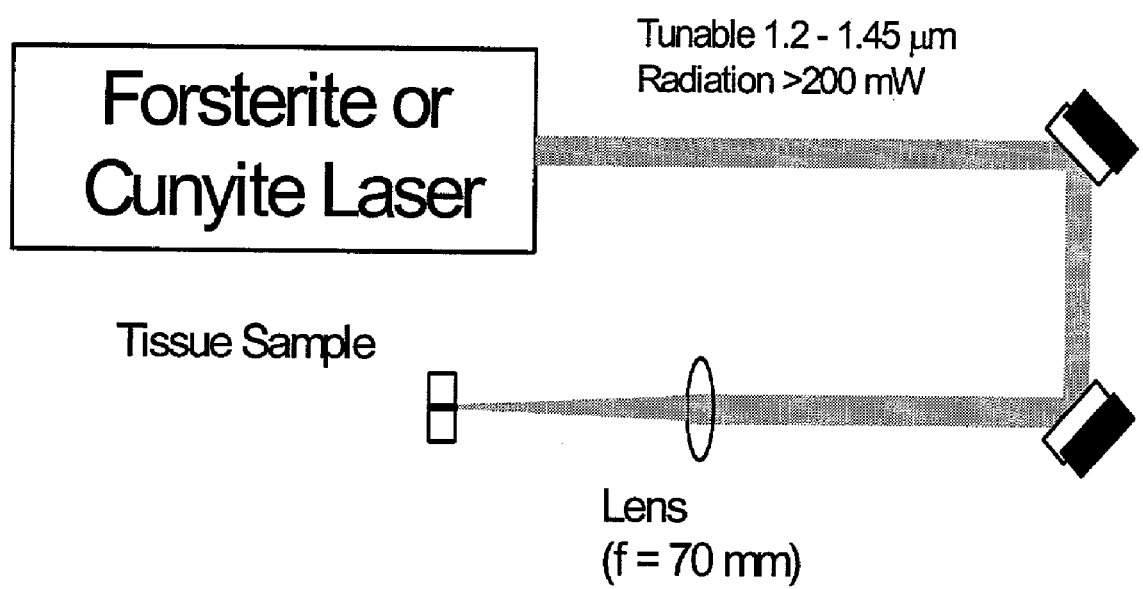
FIG. 5 is a schematic diagram of a $Cr^{4+}$ laser setup for tissue welding.

The laser setup is shown in FIG. 5. The beam was delivered in a non-contact manner. It was focused with a short focal length lens (f=70 mm) producing a spot size of 0.4 mm, positioned at 50 mm from the lens. The wavelength was measured with a spectrometer and the power output of the focus lens was measured with a power meter. The laser wavelengths which were selected for the tissue welding test were: 1,220 nm, 1,240 nm, 1,270 nm, 1,300 nm (for the Forsterite tunable laser) and 1,360 nm, 1,430 nm, (for the Cunyite tunable laser). The power output was kept at 220 mW for each. The power density was 175 W/ cm$^2$.

Shell membranes were obtained from hen eggs by carefully removing the shell and the albumin. These eggs were purchased from a local market. After washing with a 0.9% saline solution, shell membranes were kept moist at 4° C. for testing.

Figure 6:
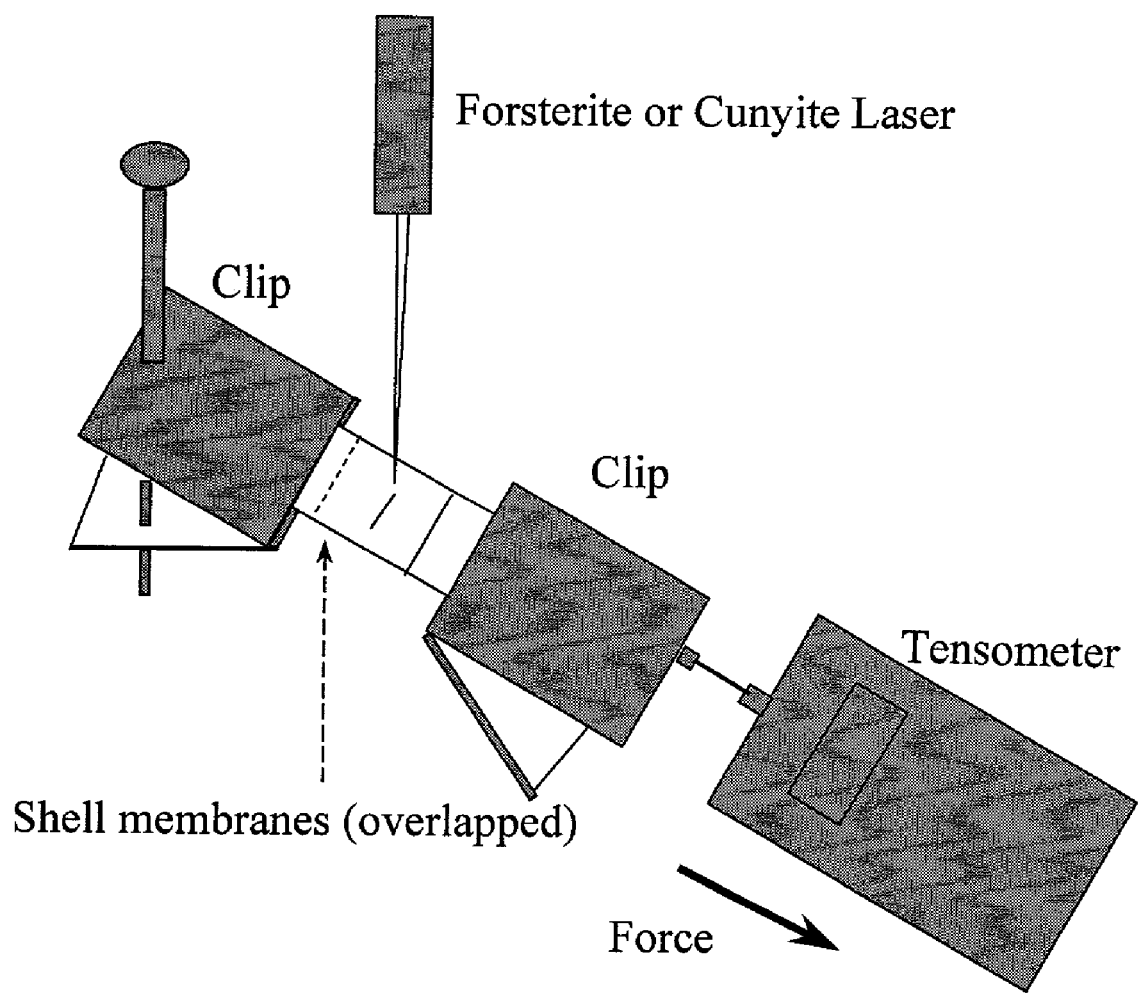
FIG. 6 is a schematic diagram of a tensile strength measurement apparatus for laser shell membrane welding.

The shell membranes were sectioned into pieces 10 mm in length and 5 mm in width. Two shell membranes were overlapped by 5 mm in length. The other two sides were gripped with clips, which were fixed to a translation stage. The general set up is set forth in FIG. 6. Laser welding was performed on the overlapped portion utilizing scanning laser irradiation. The stage was moved forward at approximately 5 mm/30 seconds, then back at the same speed and the same length. A five mm fusion line was obtained. The total exposure time was 5 mm/min. The energy fluence was 10.5 KJ/ cm$^2$.

Once the weld was completed, the welding results were tested with a digital force gauge for measuring tensile strength. The digital force gauge was connected to one side clip with the other side fixed. The tension force parallel to the fused sample surface was applied, perpendicular to the welded line, until the fusion site broke. The maximum force was recorded automatically (see FIG. 6).

Figure 11:
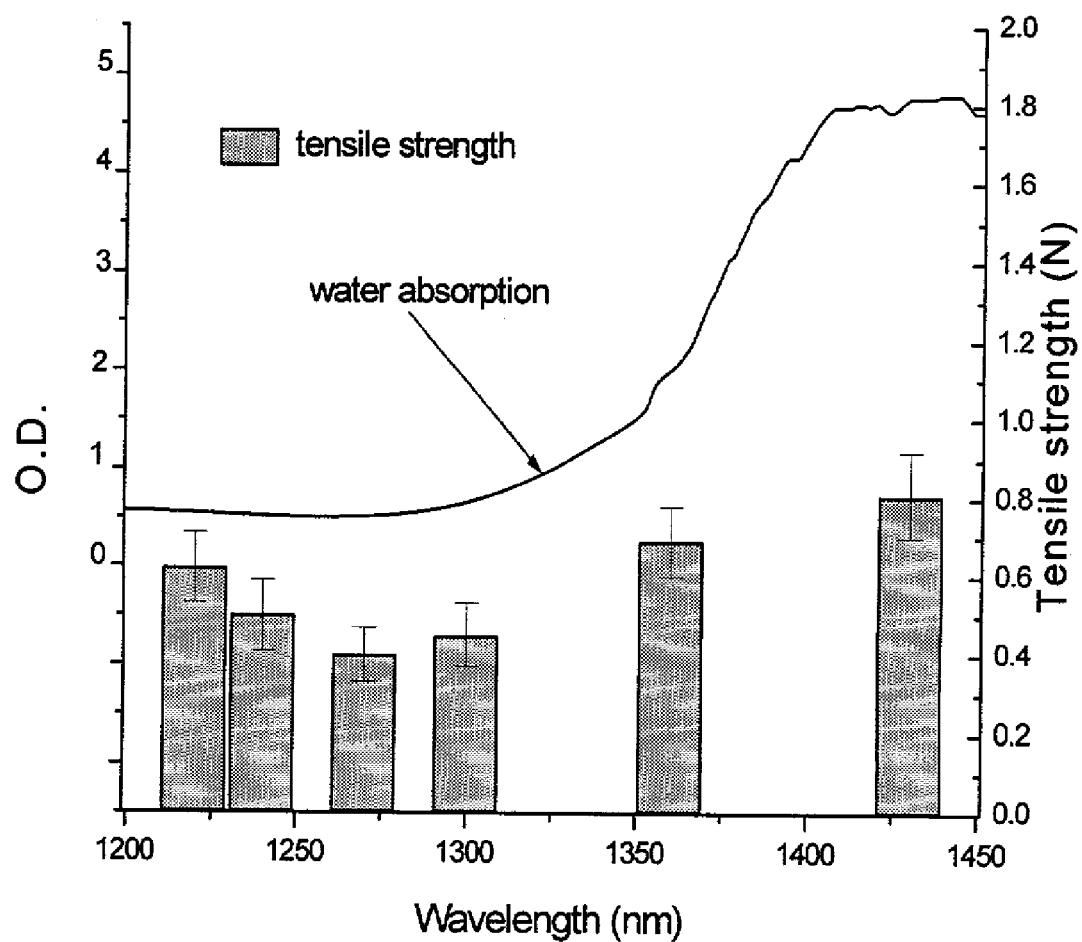
FIG. 11 is a chart showing the tensile strength for shell membrane welding and water absorption spectrum at different wavelengths.

The recorded tensile strength is plotted vs. the absorption spectrum of water for shell membranes at different wavelengths in FIG. 11. The tensile strength of shell membrane welding at wavelengths giving higher water absorption is significantly larger than that of the other sample groups. There is a relationship between tensile strength and water absorption: the higher the water absorption, the greater the tensile strength.

The end point of shell membrane welding is qualitatively described by bleaching of superficial tissue at the welded line, especially in the 1,430 nm group. The results of shell membrane welding with different wavelengths are shown below in Table 1. There are statistical differences in each group with a different wavelength but the same power intensity (F=51.35576, p≈0). The best wavelength for laser welding is 1,430 nm.

TABLE 1

Tensile strength for shell membrane welding at different wavelengths.

| Wavelengths (nm) | 1,220 | 1,240 | 1,270 | 1,300 | 1,350 | 1,430 |
|---|---|---|---|---|---|---|
| Tensile Strength (N) | 0.62 ± 0.19 | 0.50 ± 0.09 | 0.40 ± 0.07 | 0.45 ± 0.08 | 0.69 ± 0.09 | 0.81 ± 0.11 |
| p* | 0.00042 | 0.0000 | ≈0 | 0.0000 | 0.00125 | |

*Student's t-test, compared with the 1,430 nm group

EXAMPLE 5

The procedures of Example 4 were then repeated using animal skin tissue. The skin sample was harvested form etherized Wistar rats. After shaving the fur, a cut was made to obtain a tissue sample of measuring 10×10 mm. Two skin pieces were laser welded border to border with the best wavelength and the two next best wavelengths (results from Example 4). No conventional suture was performed. A 5 mm fusion line was prepared following the one minute scanning laser irradiation method of Example 4. The tensile strength was measured with the digital force gauge described in Example 4.

Differences in the tensile strength (n=15 for each group in the shell membrane welding, and n=20 for each group in the skin welding) were compared by an analysis of one side variance (ANOVA) and a Student's t test.

Figure 12:
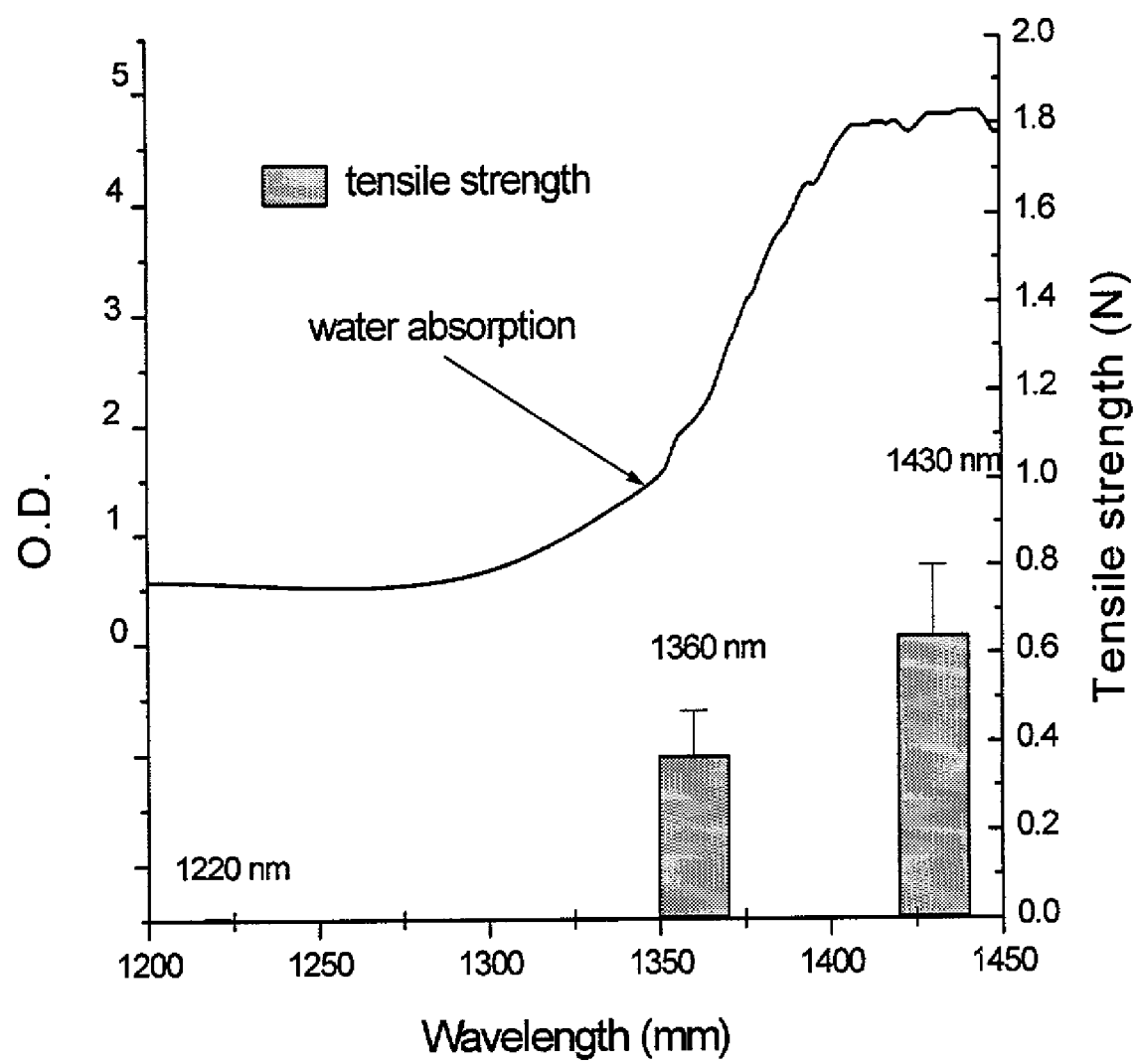
FIG. 12 is a chart showing the tensile strength for skin welding and water absorption spectrum at different wavelengths.

The laser effect on skin welding was visualized by a slight discoloration and translucence at the fusion line in the 1,430 and the 1,360 nm groups. No color changes were observed in the 1,220 nm group. The tensile strength results of skin welding with 1,430, 1,360, and 1,220 nm wavelengths are shown in FIG. 12. The average initial post-welded tensile strength values were ≈0 N for the 1,220 nm group, 0.37±0.10 N for the 1,360 nm group and 0.64±0.16 N for the 1,430 nm group. The 1,430 nm group obtained the best tensile strength with a statistical significance compared with the 1,350 nm group and the 1,220 nm group (t=6.993, p<0.01, and t=18.089, p<0.01, respectively). No welds were achievable at 1,220 nm under the same laser conditions.

The results of the above experiments demonstrate the following:

(a) Power-gel™ was formed by introducing 0.5 to 5% myristic acid into 33% gelatin at the temperature of 60° C. for one hour, using an active ester method.

(b) Gelatin and Power-gel™ as a solder are much stronger than albumin. Power-gel™ has the following characteristics: the tensile strength of 1428.15 N/cm$^2$ and of 1319.82 N/cm$^2$ in humidity; the torque strength of 1139.57 N/cm$^2$ and of 987.30 N/cm$^2$ in humidity; the best welding result obtained at the myristic acid's concentration of 0.5% to 5%; Power-gel™ has a tensile strength of up to thirteen times greater than that of a 50% albumin solution, and a torque strength of up to twelve times greater than that of a 50% albumin solution; and Power-gel™ has less water uptake ability than gelatin and better welding and thermal properties.

(c) Different welding results are obtained with the same laser conditions using different NIR wavelengths from Cr$^{4+}$ lasers. The weld strength follows the absorption spectrum of water. Selected NIR wavelengths can improve welding and avoid thermal injury to tissue with or without agents.

(d) 33% gelatin solution in PBS has a tensile strength of up to nine times greater than that of a 50% albumin solution, and a torque strength of up to ten times greater than that of a 50% albumin solution.

(e) The characteristics of Cr$^{4+}$ laser beams absorbed by water remedies the defect of gelatin's lack of an absorption peak in NIR.

(f) The tensile strength of welded tissues can be improved with the addition of gelatin or Power-gel™ as a solder when Cr$^{4+}$ laser tissue welding or sealing.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A method for welding tissue wounds in an animal, comprising:
   joining edges of a tissue wound; and
   irradiating the wound with a $Cr^{4+}$ laser, the laser being tunable continuously over a range of penetration depth in the tissue wounds, the range which corresponds to the absorption band of water in the tissue,
   whereby the laser heats tissue surrounding the wound and facilitates bonding of native tissue protein present in the tissue surrounding the wound to achieve tissue repair.

2. The method of claim 1, wherein the $Cr^{4+}$ laser is tuned to a range of between about 1,150 nm to about 1,600 nm.

3. The method of claim 1, wherein a solder is added to the edges of the tissue wound to enhance the strength of the tissue repair.

4. The method of claim 3, wherein a dye is added to the solder.

5. The method of claim 3, wherein the solder is gelatin.

6. The method of claim 5, wherein the solder is an esterified gelatin.

7. The method of claim 6, wherein the gelatin is esterified with a fatty acid.

8. The method of claim 7, wherein the fatty acid is myristic acid.

9. The method of claim 8, wherein the myristic acid comprises about 0.5 to about 5.0 weight percent of the solder.

10. The method of claim 1, wherein the animal is a human.

11. The method of claim 1, wherein the tissue wound is to tissue selected from the group consisting of skin, mucosal tissue, bone, blood vessels, neural tissue, hepatic tissue, pancreatic tissue, splenic tissue, renal tissue, bronchial tissue, tissues of the respiratory tract, tissues of the urinary tract, tissues of the gastrointestinal tract and tissues of the gynecologic tract.

12. The method of claim 11, wherein the tissue wound is a fistula of the gastrointestinal tract.

13. The method of claim 11, wherein the tissue wound is a fistula of the urinary tract.

14. The method of claim 11, wherein the tissue wound is an air leak in pulmonary tissue.

15. A method for welding tissue wounds in an animal, comprising:
   joining edges of a tissue wound;
   applying a fatty acid esterified gelatin solder to the edges of the tissue wound; and
   irradiating the wound with a laser,
   whereby the laser heats the esterified gelatin solder and tissue surrounding the wound and facilitates bonding of the estenfied gelatin solder and native tissue protein present in the tissue surrounding the wound to achieve tissue repair.

16. The method of claim 15, wherein the fatty acid is myristic acid.

17. The method of claim 16, wherein the myristic acid comprises about 0.5 to about 5.0 weight percent of the solder.

* * * * *